(12) United States Patent
Reed et al.

(10) Patent No.: US 8,986,525 B2
(45) Date of Patent: Mar. 24, 2015

(54) METHOD AND APPARATUS FOR SENSING A PROPERTY OF A FLUID

(75) Inventors: Sam Reed, London (GB); Pantelakis Georgiou, London (GB); Timothy G. Constandinou, London (GB)

(73) Assignee: DNA Electronics Limited, London (GB)

(*) Notice: Subject to any disclaimer, the term of this patent is extended or adjusted under 35 U.S.C. 154(b) by 75 days.

(21) Appl. No.: 13/820,148

(22) PCT Filed: Aug. 6, 2010

(86) PCT No.: PCT/GB2010/051299
§ 371 (c)(1),
(2), (4) Date: Mar. 1, 2013

(87) PCT Pub. No.: WO2012/017185
PCT Pub. Date: Feb. 9, 2012

(65) Prior Publication Data
US 2013/0193003 A1    Aug. 1, 2013

(51) Int. Cl.
*G01N 27/414* (2006.01)
*B01L 3/00* (2006.01)
*G01D 5/30* (2006.01)

(52) U.S. Cl.
CPC ...... *G01N 27/4148* (2013.01); *B01L 3/502707* (2013.01); *B01L 3/502715* (2013.01);
(Continued)

(58) Field of Classification Search
CPC ............. G01N 27/4148; G01N 27/414; B01L 2300/023; B01L 2300/0645; B01L 2300/0654; B01L 2300/0887; B01L 2300/0816; B01L 3/502; G01D 5/30
USPC .......... 204/403.01; 205/775; 422/68.1, 82.01; 435/287.1; 438/39
See application file for complete search history.

(56) References Cited

U.S. PATENT DOCUMENTS

| 6,182,497 B1 | 2/2001 | Krajci |
| 6,376,233 B1 | 4/2002 | Wolf et al. |

(Continued)

FOREIGN PATENT DOCUMENTS

| EP | 1 396 725 | 3/2004 |
| JP | 2001-507217 | 6/2001 |

(Continued)

OTHER PUBLICATIONS

Wilhelm Int'l Search Report for PCT/GB2010/051299, six pages, dated May 19, 2011.

(Continued)

*Primary Examiner* — Jennifer Dieterle
(74) *Attorney, Agent, or Firm* — Nixon & Vanderhye PC

(57) ABSTRACT

A device for sensing a property of a fluid comprising a first substrate having formed thereon a sensor configured in use to come into contact with a fluid in order to sense a property of the fluid, and a wireless transmitter for transmitting data over a wireless data link and a second substrate having formed thereon a wireless receiver for receiving data transmitted over said wireless link by said wireless transmitter. The first substrate is fixed to or within said second substrate. Additionally or alternatively, the device comprises a first substrate defining one or more microfluidic structures for receiving a fluid to be sensed and a second substrate comprising or having attached thereto a multiplicity of fluid sensors, the number of sensors being greater than the number of microfluidic structures. The second substrate is in contact with the first substrate such that at least one of the sensors is aligned with the or each microfluidic structure so as to provide an active sensor for the or each structure, and such that one or more of the sensors is or are not aligned with any microfluidic structure and is or are thereby redundant.

22 Claims, 5 Drawing Sheets

(52) U.S. Cl.
CPC ............... *G01D5/30* (2013.01); *B01L 2200/12* (2013.01); *B01L 2300/023* (2013.01); *B01L 2300/0645* (2013.01); *B01L 2300/0654* (2013.01); *B01L 2300/0816* (2013.01); *B01L 2300/0887* (2013.01)
USPC ............... 204/403.01; 435/287.1; 422/82.01; 422/68.1; 205/775; 438/49

(56) References Cited

U.S. PATENT DOCUMENTS

| | | | |
|---|---|---|---|
| 7,157,050 B2 * | 1/2007 | Yazawa et al. | ............... 422/68.1 |
| 7,297,913 B2 | 11/2007 | Tholl et al. | |
| 7,426,442 B2 * | 9/2008 | Gallagher | ....................... 702/32 |
| 7,438,792 B2 * | 10/2008 | Mathies et al. | ............... 204/452 |
| 7,948,015 B2 | 5/2011 | Rothberg et al. | |
| 8,264,014 B2 | 9/2012 | Rothberg et al. | |
| 8,269,261 B2 | 9/2012 | Rothberg et al. | |
| 8,306,757 B2 | 11/2012 | Rothberg et al. | |
| 8,415,716 B2 | 4/2013 | Rothberg et al. | |
| 8,426,898 B2 | 4/2013 | Rothberg et al. | |
| 8,426,899 B2 | 4/2013 | Rothberg et al. | |
| 8,441,044 B2 | 5/2013 | Rothberg et al. | |
| 8,445,945 B2 | 5/2013 | Rothberg et al. | |
| 8,492,800 B2 | 7/2013 | Rothberg et al. | |
| 8,496,802 B2 | 7/2013 | Rothberg et al. | |
| 8,502,278 B2 | 8/2013 | Rothberg et al. | |
| 8,519,448 B2 | 8/2013 | Rothberg et al. | |
| 8,530,941 B2 | 9/2013 | Rothberg et al. | |
| 8,575,664 B2 | 11/2013 | Rothberg et al. | |
| 8,658,017 B2 | 2/2014 | Rothberg et al. | |
| 8,685,230 B2 | 4/2014 | Rothberg et al. | |
| 2004/0121354 A1 | 6/2004 | Yazawa et al. | |
| 2006/0020371 A1 * | 1/2006 | Ham et al. | .................... 700/266 |
| 2006/0191318 A1 | 8/2006 | McBride et al. | |
| 2007/0096165 A1 | 5/2007 | Lipisko et al. | |
| 2008/0205497 A1 | 8/2008 | Kahlman et al. | |
| 2009/0127589 A1 | 5/2009 | Rothberg et al. | |
| 2010/0188073 A1 | 7/2010 | Rothberg et al. | |
| 2010/0197507 A1 | 8/2010 | Rothberg et al. | |
| 2011/0263463 A1 | 10/2011 | Rothberg et al. | |
| 2012/0034607 A1 | 2/2012 | Rothberg et al. | |
| 2012/0037961 A1 | 2/2012 | Rothberg et al. | |
| 2012/0040844 A1 | 2/2012 | Rothberg et al. | |
| 2012/0108456 A1 | 5/2012 | Frey et al. | |
| 2012/0129703 A1 | 5/2012 | Rothberg et al. | |
| 2012/0129728 A1 | 5/2012 | Rothberg et al. | |
| 2012/0129732 A1 | 5/2012 | Rothberg et al. | |
| 2012/0135870 A1 | 5/2012 | Rothberg et al. | |
| 2012/0279859 A1 | 11/2012 | Rothberg et al. | |
| 2012/0280285 A1 | 11/2012 | Rothberg et al. | |
| 2012/0280286 A1 | 11/2012 | Rothberg et al. | |
| 2012/0283146 A1 | 11/2012 | Rothberg et al. | |
| 2012/0286332 A1 | 11/2012 | Rothberg et al. | |
| 2012/0286333 A1 | 11/2012 | Rothberg et al. | |
| 2012/0286771 A1 | 11/2012 | Rothberg et al. | |
| 2012/0288853 A1 | 11/2012 | Rothberg et al. | |
| 2012/0288976 A1 | 11/2012 | Rothberg et al. | |
| 2012/0289413 A1 | 11/2012 | Rothberg et al. | |
| 2012/0293158 A1 | 11/2012 | Rothberg et al. | |
| 2012/0295795 A1 | 11/2012 | Rothberg et al. | |
| 2012/0322054 A1 | 12/2012 | Rothberg et al. | |
| 2013/0264611 A1 | 10/2013 | Rothberg et al. | |
| 2013/0292743 A1 | 11/2013 | Rothberg et al. | |

FOREIGN PATENT DOCUMENTS

| | | |
|---|---|---|
| JP | 2004-101253 | 4/2004 |
| JP | 2010-019570 | 1/2010 |
| JP | 2010-513869 | 4/2010 |
| JP | 2012-522230 | 9/2012 |
| WO | 01/14873 | 3/2001 |
| WO | 2009/045092 | 4/2009 |
| WO | 2010/047804 | 4/2010 |

OTHER PUBLICATIONS

Wilhelm Written Opinion for PCT/GB2010/051299, six pages, dated May 19, 2011.
Wilhelm International Preliminary Report on Patentability for PCT/GB2010/051299, 11 pages, dated Nov. 30, 2012.

* cited by examiner

METHOD AND APPARATUS FOR SENSING A PROPERTY OF A FLUID

This application is the U.S. national phase of International Application No. PCT/GB2010/051299, filed 6 Aug. 2010, which designated the U.S.; the entire content of which is hereby incorporated by reference.

FIELD OF THE INVENTION

The present invention relates to methods and apparatus for sensing a property of a fluid. In particular, the invention provides coordination of sensors in a microfluidic environment.

BACKGROUND

Devices that integrate one or several functions on a single chip have many applications such as monitoring a property of a fluid or a chemical reaction. Such devices, known as lab-on-chip devices, typically combine semiconductor sensors and microfluidic channels on a tiny scale.

However, there is a requirement for low-cost integration of different technologies, in particular CMOS/MEMS and microfluidics. Economies-of-scale especially driven by the semiconductor industry favour solutions based on unmodified commercial processes. The constraints dictated by the varying range of physical dimensions of the different components make wafer-level integration too costly for low-cost mass manufacture. For example, a typical Lab-on-Chip application may require CMOS components having an area in the region of 1-10 $mm^2$, MEMS components in the region of 25-100 $mm^2$ and microfluidics components in the region of 200-2500 $mm^2$. Therefore integrating these at wafer level would be hugely wasteful to CMOS/MEMS technologies, as the common Lab-on-Chip area would be dominated by the requirements of interfacing fluids and external systems to the devices.

FIG. 1 of the accompanying drawings shows a cross-section of hybrid CMOS/microfluidics composite having bond-wires 10 and die 4 encapsulated using photo-patternable epoxy 2. The microfluidic chamber 11 is formed by the substrate 1 being fixed to the carrier substrate 8. Problems arise in wire-bonding the fine bond wires and the need to encapsulate them afterwards.

Encapsulating chips at die level typically requires depositing and processing photosensitive materials (such as certain epoxies and SU-8) onto composite assemblies (such as a package or substrate), which are wire-bonded to the die (see FIG. 1 of the accompanying drawings). A common challenge is to avoid damage to delicate bond-wires due to mechanical stress caused by fluid viscosity in addition to centrifugal forces in spin-coating. An alternative approach is to define the unexposed (i.e. chemical sensitive) area via a sacrificial material (eg. SU-8), or by accurately defining a frame and then potting the region between the frame and package using a UV-curable epoxy. This technique is often referred to as "Dam and Fill" encapsulation. Commercial chemical sensors use more complex process flows based on combining the above techniques with pre-fabricated housings to ensure robust isolation in addition to long-term stability. However these are very laborious and thus expensive to mass-produce. All these above-mentioned techniques however have two fundamental limitations: (i) an unwanted well (typically 200-300 µm depth) is formed inside the bondpad regions, and (ii) due to this relatively thick encapsulant build-up, the top surface is not perfectly planar. This causes sealing, adhesion, and alignment problems when overlaying microfluidic channels above, which often requires an intermediate levelling step.

Several technology-based packaging solutions have been proposed. However these typically require post-processing CMOS devices at wafer scale (i.e. before dicing). Flip-chip packaging methods can provide a robustly encapsulated, planar top surface, however the issue of "parasitic wells" above the chip surface is not overcome. The MIT/Lincoln Labs experimental 3D CMOS process based on multiple Silicon-on-Insulator (SOI) CMOS tiers allows for through-tier vias and since the silicon sits on an insulating substrate, the bondpads can be brought to the underside of the substrate, leaving the top-layer planar for chemical sensing purposes. This perhaps offers the most promising solution for future emerging technologies (expected to feature towards the end of Moore's law—when scaling from 22 nm to 10 nm). This is confirmed by IBM dedicating a complete issue to 3D CMOS in their flagship "IBM Journal of Research & Development". However, this technology remains years from being commercially available, and even then is expected to remain relatively expensive (compared to bulk CMOS) and thus it will be limited to niche applications.

Once the sensor has been encapsulated, it is desirable to provide a microfluidic channel to bring the fluid to the sensor. These channels are typically formed in a substrate, which is separate from the sensor substrate. The two substrates are aligned and sealed to each other. As semiconductor sensors become progressively smaller with a finer pitch, there arise problems with aligning the microfluidic channels to the sensors. Poor assembly tolerances mean that there is a chance that the walls between the channels may obstruct a sensor and indeed there may not be a sensor in each channel. In mass production, microfluidic alignment tolerances may be 100-1000 times more than the minimum feature size of the sensor.

In some applications it may be desirable to monitor reactions in a number of fluidic chambers using ISFET sensors. It is desirable to pattern a number of ISFET sensors on a single silicon chip, and yet have different reactions happen above each sensor. This means that the surface of the chip must be encapsulated in such a way as to create multiple chambers which are fluidically sealed from each other so that their chemical components cannot intermix.

To provide a seal between sensors, it is expected that a layer of fluidic channels/chambers will be mounted on top of the electronic chip. This could be built or etched directly on the surface of the chip with photolithography, or alternatively could be built as a separate part via a variety of means and then attached to the chip as a subsequent step.

Either way, an apparent trade-off is created as the fluidic channels/chambers must be aligned to the sensors. There is incentive to make the sensors closely spaced, i.e. fine-pitched, to minimise the size and therefore cost of the silicon chip (and fluidics as well). However, there is a competing incentive to make the sensors further apart so that it is simpler to produce the fluidics and align them with the sensors.

Substrates are often aligned by either aligning one substrate to a datum line on the other (perhaps a physical protrusion) or by aligning visually overlapping marks on each substrate. The intention is that the two substrates are centre aligned or normally aligned, such that the chambers and sensors are symmetrically aligned about a centre line(s). This usually means that the midpoint of each sensor is aligned to the midpoint of each chamber. Thus the alignment tolerance from centre is usually the width of the chamber less the sensor width, after which point a portion of the sensing surface will not be exposed to the chamber. The alignment tolerance may be expressed as:

$$\text{Tolerance} = \pm (Wc - Ws)/2 \qquad (1)$$

Where Wc,Ws represent respectively the Width of one chamber, Width of one sensor.

The following references provide background to lab-on-chip packaging:

U.S. Pat. No. 7,033,910: Method of fabricating multi layer MEMS and microfluidic devices on a substrate with layers of predetermined weak and strong bond regions, communication provided by edge interconnects between layers U.S. Pat. No. 6,910,268: Method for fabricating an IC interconnect system including an in-street integrated circuit wafer via. Not wireless, uses wired vias.

U.S. Pat. No. 7,207,728: Optical bond-wire interconnections and a method for fabrication thereof. Optical bond-wire interconnections between microelectronic chips, wherein optical wires are bonded onto microelectronic chips.

U.S. Pat. No. 6,443,179: Packaging of electro-microfluidic devices. Electrical connection is made to bond pads on the front of the MIC.

U.S. Pat. No. 6,531,342: Method for transverse hybrid loc package

U.S. Pat. No. 6,882,033: High density direct connect LOC assembly

U.S. Pat. No. 6,136,212: Polymer-based micro-machining for microfluidic devices (WO/2003/107043) OPTOELECTRONIC ASSEMBLY WITH EMBEDDED OPTICAL AND ELECTRICAL COMPONENTS.

IPC8 Class: AH05K714FI, USPC Class: 361796: Interconnection and Packaging Method for Biomedical Devices with Electronic and Fluid Functions E. Culurciello et. Al, "Capacitive Inter-Chip Data & Power Transfer for 3-D VLSI", IEEE TCAS-II, Vol. 53, No. 12, 2006.

T. D. Strong, "Integrated Electrochemical Neurosensors", IEEE ISCAS'06, pp. 4110-4113, 2006.

W. Oelβner, et al., "Encapsulation of ISFET sensor chips", Sensors & Actuators B, Vol. 105, pp. 104-117, 2005.

L. Sudakov-Boreysha et al., "ISFET CMOS Compatible Design and Encapsulation Challenges", IEEE Conference on Electronics, Circuits and Systems (ICECS'04), pp. 535-538, 2004.

"3D Chip Technology", IBM Journal of Research and Development, Vol. 52, No. 6, 2008.

Vilches A, Sanni A, Toumazou C, Single coil pair transcutaneous energy and data transceiver for low power bio-implant use, IET ELECTRONICS LETTERS, 2009, Vol: 45, Pages: 727-U25, ISSN: 0013-5194.

It is an object of the present to provide apparatuses and methods overcoming the problems with the present techniques as discussed above.

SUMMARY OF THE INVENTION

According to a first aspect of the invention there is provided a device for sensing a property of a fluid, the device comprising a first substrate having formed thereon a sensor configured in use to come into contact with a fluid in order to sense a property of the fluid, and a wireless transmitter for transmitting data over a wireless data link; and a second substrate having formed thereon a wireless receiver for receiving data transmitted over said wireless link by said wireless transmitter. The first substrate is fixed to or within said second substrate.

According to a second aspect of the invention there is provided a method of operating one or more sensors and comprising the steps of providing a fluid in contact with a sensor, powering the sensor and transmitter using a transducer, sensing a property of the fluid using the sensor, and wirelessly transmitting sensed or processed sensed data using a transmitter.

According to a third aspect of the invention there is provided a method of fabricating a microfluidic sensor device comprising the steps of providing a first substrate defining one or more microfluidic structures for receiving a fluid to be sensed, providing a second substrate comprising or having attached thereto a multiplicity of fluid sensors, the number of sensors being greater than the number of microfluidic structures, and fixing the first and second substrates together such that at least one of the sensors is aligned with the or each microfluidic structure so as to provide an active sensor for the or each structure, and such that one or more of the sensors is or are not aligned with any microfluidic structure and is or are thereby redundant.

According to a fourth aspect of the invention there is provided a device comprising a first substrate defining one or more microfluidic structures for receiving a fluid to be sensed and a second substrate comprising or having attached thereto a multiplicity of fluid sensors, the number of sensors being greater than the number of microfluidic structures. The second substrate is in contact with the first substrate such that at least one of the sensors is aligned with the or each microfluidic structure so as to provide an active sensor for the or each structure, and such that one or more of the sensors is or are not aligned with any microfluidic structure and is or are thereby redundant.

According to a fifth aspect of the invention there is provided a method of configuring a device and comprising the steps of (i) detecting a first signal corresponding to a first sensor and (ii) determining which sensors are exposed to which microfluidic structure using the first signal and knowledge of a property of the fluid of at least one microfluidic structure or knowledge of the spatial relationship among the sensors.

According to a sixth aspect of the invention there is provided a configuration apparatus for configuring a device, the configuration apparatus comprising (i) a receiver for detecting a first signal corresponding to a first sensor and (ii) means for determining which sensors are exposed to which microfluidic structure using knowledge of a property of the fluid in at least one of the microfluidic structures or knowledge of the spatial relationship among the sensors.

Preferred embodiments are set out in the accompanying dependent claims.

DESCRIPTION OF DRAWINGS

Specific embodiments of the invention will now be described by way of example only, with reference to the accompanying figures, in which.

DETAILED DESCRIPTION

Figure 2:
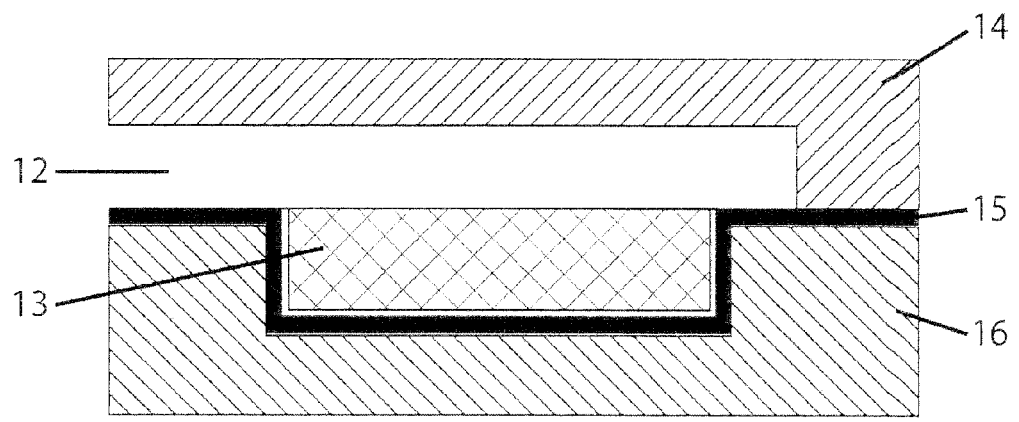
FIG. 2 is a cross-section of a microfluidic assembly with a CMOS sensor embedded within a substrate.

In one embodiment, illustrated by FIG. 2, a semiconductor sensor chip 13 is encapsulated by adhesive 15 within a recess of substrate 16. This leaves the sensing surface of the chip co-planar with the chamber 12. A second substrate 14 is sealingly fixed to the substrate 16 and provides microfluidic channels for the fluid to be sensed.

Fluid may be brought into contact with the sensing surface of chip 13 and detected. Properties such as temperature, pH, chemistry, flow conductivity, etc. may be detected by an appropriate sensor integrated into the chip. By providing suitable wireless communication and transducer hardware on the CMOS chip, a scheme for contactless power and data transfer can be implemented. The chip is thus capable of wirelessly transmitting a signal to a receiver located nearby. The signal contains data relating to the state of the chip or a property of the fluid via the sensor.

The embodiment thus provides a method of encapsulating and interfacing a sensor chip to a device without any bond-wires leaving the chip's top surface planar.

A transducer is a device for transforming energy from one form to another. For example, a circuit may receive incident radiated energy and transform it into a DC electrical power. In such a way power may be transmitted wirelessly.

Wireless communication refers to communication amongst two or more devices without the use of electrically conducting wires, as is typical of conventional communication methods. The transmission of wireless communication may be provided by energizing a signal which emanates from the transmitter or modulating an energized signal passing near or through the transmitter to create a new signal. The signal contains coded or uncoded data that can be interpreted by a receiver. The communication may be two-way in which case each device is configured to transmit and receive signals (a transceiver). A first device may produce a energy burst to request data (by polling or 'pinging') from a second device such that the second device then transmits data.

A wireless scheme may be applied to a Lab-on-Chip (LOC) assembly by implementing the following design points:
  Fit a CMOS die within a recess of a (carrier) substrate, which may be a multi-layer printed circuit board (PCB), such that the top surfaces of the die and (carrier) substrate are co-planar (see FIG. 2).
  Stack a microfluidic substrate onto the carrier substrate. These can be designed to be of equal dimensions (i.e. length and width), to form a 2-layer assembly (see FIG. 2).
  Provide a communication subsystem and transducer on the CMOS chip to recover power and data from an external source, in addition to being able to transmit data off-chip.
  Provide suitable structures, for example, PCB patterned antennas or inductors into the (carrier) substrate or sub-miniature surface mount (chip) components (depending on the wireless technique chosen) embedded within the carrier substrate.
  Provide a ground plate on the underside (obverse of the sensing surface) of the die which contacts a ground plate of the substrate for the purpose of providing an electrical ground for the die. The contacts may be bonded together by electrically conducting epoxy, which also serves to mechanically couple the die to the substrate.

Such a device has advantages of reliability, cost reduction, and ease of assembly.

A wireless sensor system arrangement alleviates the requirement for wire-bonding thus providing substantial cost benefits for mass manufacture. In addition to direct savings relating to wire-bond processing, additional processing steps are saved, for example bond-wire encapsulation and surface levelling steps. As the encapsulant around the bond wires is typically the first component to degrade when immersed in an electrolyte, the stability and reliability of the chip are also improved. The semiconductor chip itself, which requires expensive material and processing, may be much smaller than before as no space is required for bonding or encapsulation. The chip may be as small as the sensor and communication hardware.

Simplifying the process flow alleviates the requirement for time-intensive high precision alignment tasks. This means the various components can be manufactured to utilise inexpensive mass production techniques, for example injection moulding and robot assembly. Assembly alignment issue are reduced because the sensor chips may be dropped directly into the microfluidic chambers (which is physically larger than the chip itself) without the need to align the substrates exactly. There may be many chambers formed in a substrate, with one or more chips located within each chamber.

This method avoids the formation of parasitic wells formed within encapsulated dies (via traditional methods). This simplifies the microfluidic channel design, in addition to providing a means for robust substrate integration due to inherently planar substrates.

Figure 1:
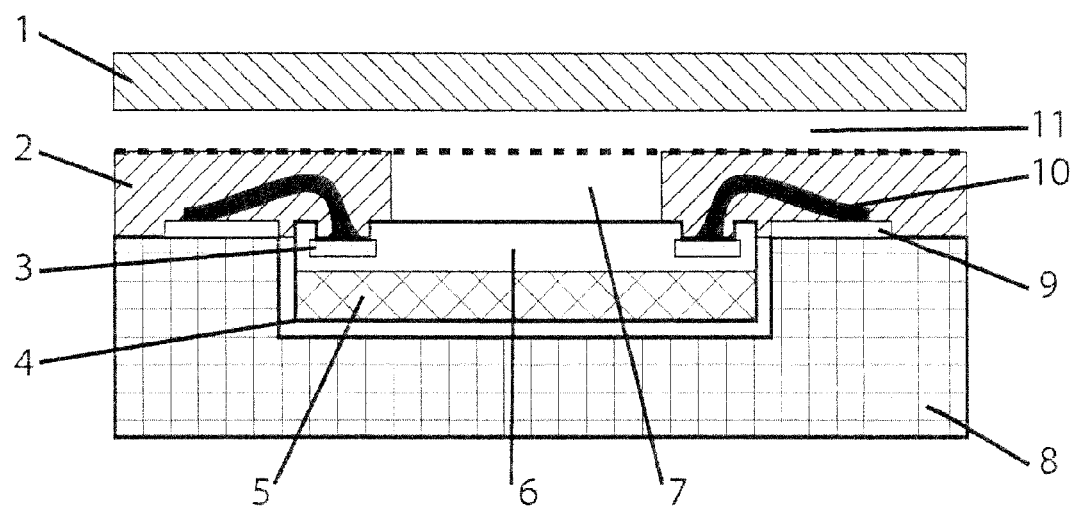
FIG. 1 is a known CMOS encapsulation method for chemical sensing.

FIG. 1 identifies the following components:
 1. Microfluidic substrate
 2. Encapsulant
 3. Bondpad (on chip)
 4. Die (i.e. chip)
 5. Silicon substrate
 6. Dielectric/Passivation
 7. Parasitic microfluidic well
 8. Carrier substrate (e.g. PCB)
 9. Bondpad (on carrier substrate)
 10. Bondwire
 11. Microfluidic channel FIG. 2 identifies the following components:
 12. Microfluidic channel
 13. Die (i.e. chip)
 14. Microfluidic substrate
 15. Adhesive/encapsulant
 16. Carrier substrate (e.g. PCB)

Figure 3:
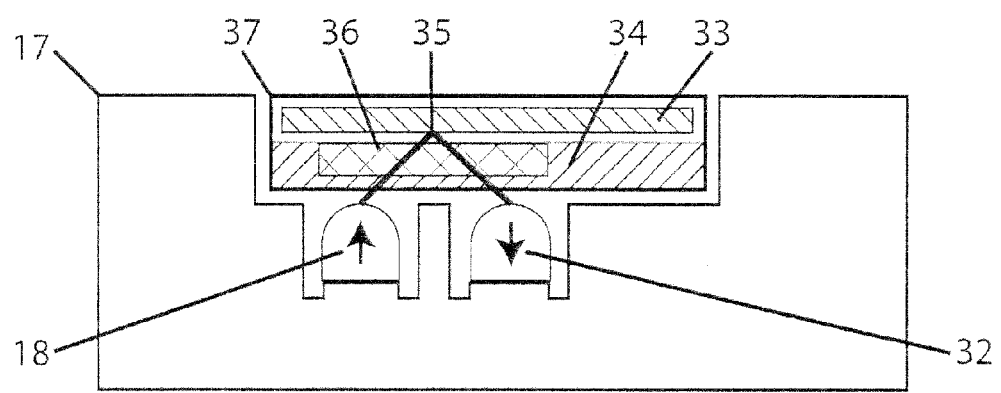
FIG. 3 illustrates an embodiment providing data transfer using optical (IR) communication.

FIG. 3 identifies the following components:
 17. Carrier substrate (e.g. PCB)
 18. Light emitter
 32. Light detector
 33. Reflector (e.g. sheet of interconnect metal)
 34. Silicon substrate
 35. Reflected light path
 36. Optical modulator
 37. Die (i.e. chip)

Figure 4:
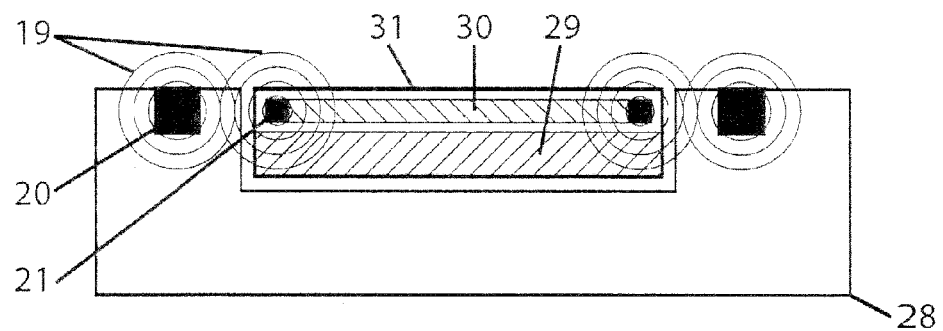
FIG. 4 illustrates an embodiment providing data transfer using local inductive coupling.

FIG. 4 identifies the following components:
 19. Inductive coupling
 20. Inductor on carrier substrate
 21. Inductor on chip
 28. Carrier substrate (e.g. PCB)
 29. Silicon substrate
 30. dielectric stack/interconnects
 31. Die (i.e. chip)

Figure 5:
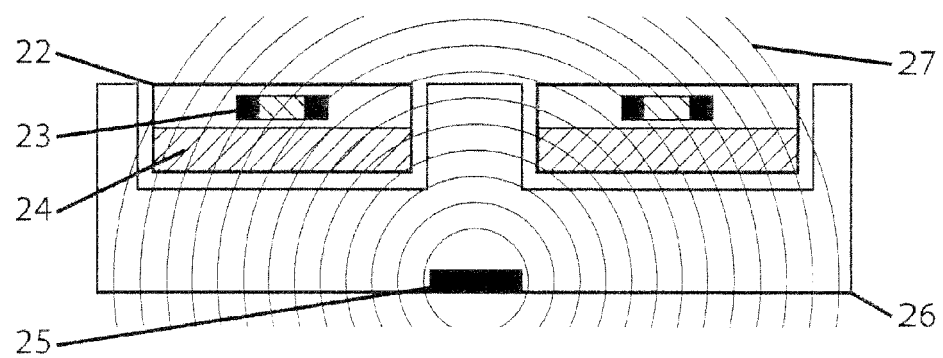
FIG. 5 illustrates an embodiment providing data transfer using RFID technology.

FIG. 5 identifies the following components:
22. Die (i.e. chip)
23. Antenna on chip
24. Silicon substrate
25. Antenna on carrier substrate
26. Carrier substrate (e.g. PCB)
27. RF communication FIGS. 3 to 5 illustrate embodiments for achieving power and data transfer (between the CMOS die and the substrate), replacing physical wire bonds with wireless methods. The figures illustrate: (FIG. 3) use of an optical emitter from the underside to power the device and use of electro-optical techniques to modulate the reflected signal; (FIG. 4) an inductive power/data transfer between on-chip and PCB inductors; and (FIG. 5) use of RF wireless technology.

The wireless power/data transfer can, for example, be achieved using the three following techniques:

Optoelectronic Transmission:

Optoelectronics is the application of electronic devices that source, detect and control light, for example by absorption and modulation of optical energy. By embedding the integrated circuit within a substrate that incorporates suitable optoelectronic components, power can be transmitted to the integrated circuit (IC) and data received from it, providing the appropriate hardware is integrated within the IC. More specifically this would require integrating a solar cell to recover optical power, in addition to an optical emitter or modulator for transmitting the sensor data. One method of achieving the latter is by modulating free-carrier absorption through reverse biasing a pn-junction (see UK patent application 1001696.2). This scheme is illustrated in FIG. 3. The carrier substrate (17) houses an optical emitter (18), optical detector (32) and integrated circuit (37). By irradiating a modulator (36) designed within the bulk silicon (34), the resulting beam of light (35) can be modulated by adjusting the absorption within the modulator. The resulting beam can be reflected to the underside of the IC using a metallic reflector (33). This additionally acts to double the modulation effect (by modulating the light twice—the incident and return path).

Near Field:

Near field wireless transmission techniques work over distances comparable to, or a few times the diameter of the device(s), and up to around a quarter of the wavelengths used. Near field transfer is usually magnetic (inductive), but electric (capacitive) energy transfer can also occur.

Power and data can alternatively be transmitted wirelessly through inductive coupling between an on-chip inductor and patterned inductor embedded within the carrier substrate. This is illustrated in FIG. 4. The integrated circuit (31) incorporates the sensor, interface electronics and integrated inductor (21). The integrated inductor is designed using appropriate geometries of metallic interconnects (30) within the chip. This is inductively coupled (19) to a secondary inductor (20) embedded within the carrier substrate (28) designed such as to maximize the coupling efficiency (e.g. in close proximity, matched quality factors, etc.). The integrated circuit (31) and carrier substrate (28) are also required to include all necessary components to facilitate the inductive transfer of power and data via standard circuit topologies.

Far Field:

Far field methods achieve longer ranges, often multiple kilometer ranges, where the distance is much greater than the diameter of the device(s). With Electo-Magnetic propagation, signals may be transmitted from multiple integrated circuits within a single carrier substrate employing far-field (e.g. traditional RF) transmission of power and data. Within each integrated circuit (22), an integrated antenna (23) is included in addition to a standard RF transceiver circuit. The carrier substrate (26) includes an embedded antenna (25) which is shared by all IC's by transmitting a carrier wave from the substrate antenna (25), receiving this on the integrated antennas (23) and rectifying the AC signal to recover a DC power supply. Data is transmitted from the independent chips back to the carrier by implementing on-chip RF transmitters. Multiple channels (for multiple chips) can be multiplexed by using standard RF communication techniques (time-division, frequency division, etc. multiplexing). The system can either use a shared set of antennas for power and data transmission or separate elements to improve the efficiency of each task (i.e. power and data transfer).

Thru-Fluid Propagation:

A signal can be transmitted through the fluid. It is well-known that a water solution which includes salt, or any other effective electrolyte, acts as a conductive medium, and therefore can be used to send information on the same principle as a wire. One illustrative implementation is to have a chip with an integral electrode (e.g. silver/silver chloride or other means) which contacts the fluid, allowing the circuitry on the chip to interface with the potential of the fluid and/or vice-versa. A second electronic module in communication with the chip would also have an electrode contacting the same electrolyte. Any voltage or voltage change driven by an electrode on either module would be conducted to the other module by the fluid, thereby influencing the other electrode being measured at the receiver. In this way, voltage changes could act as a signal for analogue or digital information to be sent between the modules via the potential of the fluid. An alternative to direct electrode contact is to capacitively-couple the chip to the fluid (for example, if a metal trace in the chip was separated from direct contact with the fluid by chip passivation) or by other non-contact means.

Further, if it is desirable for the fluid to also act as a stable DC bias (as in the case of a potentiometric measurement), then the circuitry, electrodes, and or signals, can be designed such as to only affect the potential of the fluid within a particular frequency range which does not interfere with the DC bias. Generally, having a non-zero-impedance coupling between the electrode and the fluid, or between the driving circuit and the electrode, in at least one frequency band, is one way to ensure that the driving circuit can influence the fluid's potential without completely excluding the influence of other sources. This would enable 2-way communication, or multiplexing of multiple sources (e.g. via different frequency ranges or many other known techniques for multiplexing RF signals). One such implementation would be to have a capacitor in series between the driving circuit and the reference electrode in order to act as a high-pass filter, allowing the DC potential to be set externally by a reference electrode or any other module in the system (which correspondingly may have a low-pass filter with non-zero source impedance at some frequencies in its driving circuit to allow the electrolyte's potential to be driven at relatively higher-frequency for data communication). Another enhancement would be for the chip to connect both driving and receiving circuits to its electrode via non-zero and non-infinite impedances, such that both send and receive functions are possible. Tri-state buffers can be used to further eliminate the influence of the driving circuit when not desirable.

The above embodiments differ from prior art wireless devices in several respects:

The wireless elements are all combined in a monolithic integrated circuit (IC), as opposed to being implemented using one or more discrete components (eg. off-chip antenna, inductor, etc.

The integrated circuit (IC) contains no bondpads or bondwire connections, whereas other devices are wireless in one aspect but still rely on bondwires in other aspects, for example between the chip and package for power supply or off-chip discrete components.

The transmitter and receiver communicate wirelessly whilst being physically connected. The distance between them is also predetermined and substantially fixed. Typically the reason for using wireless technology is because the transmitter and receiver are physically separated and occupy positions that change or are unknown.

In one embodiment, a fluid is introduced into a chamber of the device and brought into contact with the sensor surface. The sensor is used to detect a property of the fluid or monitor a reaction within the fluid. This property may be the temperature or ion concentration. The carrier substrate may be constantly powering the device and/or waiting to receive a signal. The chip could transmit the present sensor value, possibly after performing signal processing. Alternatively the substrate would transmit power at a desired time which would power up the sensor chip. The chip may send the signal immediately or wait until it receives a request for the signal. For example, there may be several sensors monitoring separate fluids and the device could poll or ping the individual sensors at predetermined times.

The power transmitter, signal transmitter, and signal receiver may be formed on the same substrate or separated. For example the substrates may be plugged as a cartridge into an In Vitro Device having circuitry which receives, analyses, and displays the sensor value.

Preferably the chip is monolithic comprising the sensor(s), transducer, and transmitter circuitry. Therefore there is provided an integrated chip having no wires between the chip and a substrate.

In one preferred embodiment there is a chip in physical contact with and wirelessly communicating with a PCB substrate. The chip has:

A receiving coil with a tuning capacitor to impedance-match the transmitting coil and optimise the quality factor.

An asynchronous rectifier to rectify the output of the receiving coil to give a stable DC output voltage (1.4 V with 0.1 V ripple).

A clock recovery circuit in the form of a phase-locked loop (PLL) which comprises a voltage-controlled oscillator (VCO), a phase detector, and a loop filter. This produces a clock signal synchronized with the transmitting frequency.

A BPSK demodulator which uses the aforementioned on-chip recovered clock signal and the voltage across the receiving coil to produce the demodulated bitstream.

The PCB substrate has a transmitting coil driven with a 60 V peak-to-peak drive voltage in the 2.4 GHz unlicensed band. The data is coded onto this voltage using binary phase-shift keying (BPSK) such that the driving amplitude, and hence the power transmitted to the chip, is constant Data is transmitted from the chip to the PCB via the on-chip "receiving" coil to the PCB "transmitting" coil (i.e., there are no separate coils). This is done via load-shift keying (LSK) in which the load the on-chip coil sees is changed. This causes the current oscillating in the PCB coil to change, which can easily be measured and demodulated.

In a further embodiment, microfluidic structures are finely-spaced without requiring fine alignment, by building redundancy into the system by creating an array of ISFETs which are greater in number than the microfluidic structures themselves. Then, within wide tolerance in lateral alignment, the redundancy ensures that wherever each microfluidic structure aligns during assembly, at least one ISFET will be available at an appropriate location to measure it. The ISFETs which align with the microfluidic structures are utilised and the ones that are buried under walls are not.

In an embodiment, illustrated by FIG. 6a, an array of sensors 42 are fixed to one substrate, and a second substrate 40 comprising an array of microfluidic chambers 41 is aligned and sealed to the first substrate. The sealing prevents fluids from one chamber entering another chamber. In order to provide a robust assembly procedure, there are more sensors than chambers, the sensor being arranged such that relative misalignment of the two substrates still results in at least part of one sensing surface exposed to the fluid in each chamber.

As can be seen from FIG. 6a, chambers 41a illustrate the case where chambers are well aligned with one whole sensor each. However the substrates may be relatively misaligned in the X and/or Y direction such that each chamber (indicated by dashed chambers 41b) is aligned with a different sensor, or portions of several sensors.

The amount of movement permissible in the plane of the substrate will depend largely on the number of excess sensors and pitch of the sensors. In FIG. 6a, the sensor pitch is equal to the width of the chamber allowing the greatest amount of movement whilst ensuring that each chamber is aligned with a whole sensor or portions of several sensors. This arrangement is suitable to sensors that do not require that the entire sensing surface be exposed to the fluid in order to make a measurement.

For sensors that require that the entire sensing surface be exposed to the fluid, it will be desirable to decrease the pitch of the sensors. As seen in FIG. 6b, each chamber aligns with at least one whole sensor and possibly portions of additional sensors. In this arrangement it is possible to have a chamber aligned with 4 whole sensors, the sensor pitch arranged such that the sensor pitch plus one sensor width is less than or equal to the chamber width.

It is possible that in addition to alignment tolerance, one would consider the manufacturing tolerances of the chambers or sensors. For example the chamber array may be irregularly spaced apart or have differing chamber widths. The combination of these tolerances should be considered when determining the sensor layout. In particular, the alignment tolerance will affect the number of excess sensors needed and the manufacturing tolerance will affect the sensor pitch needed.

Figure 6:
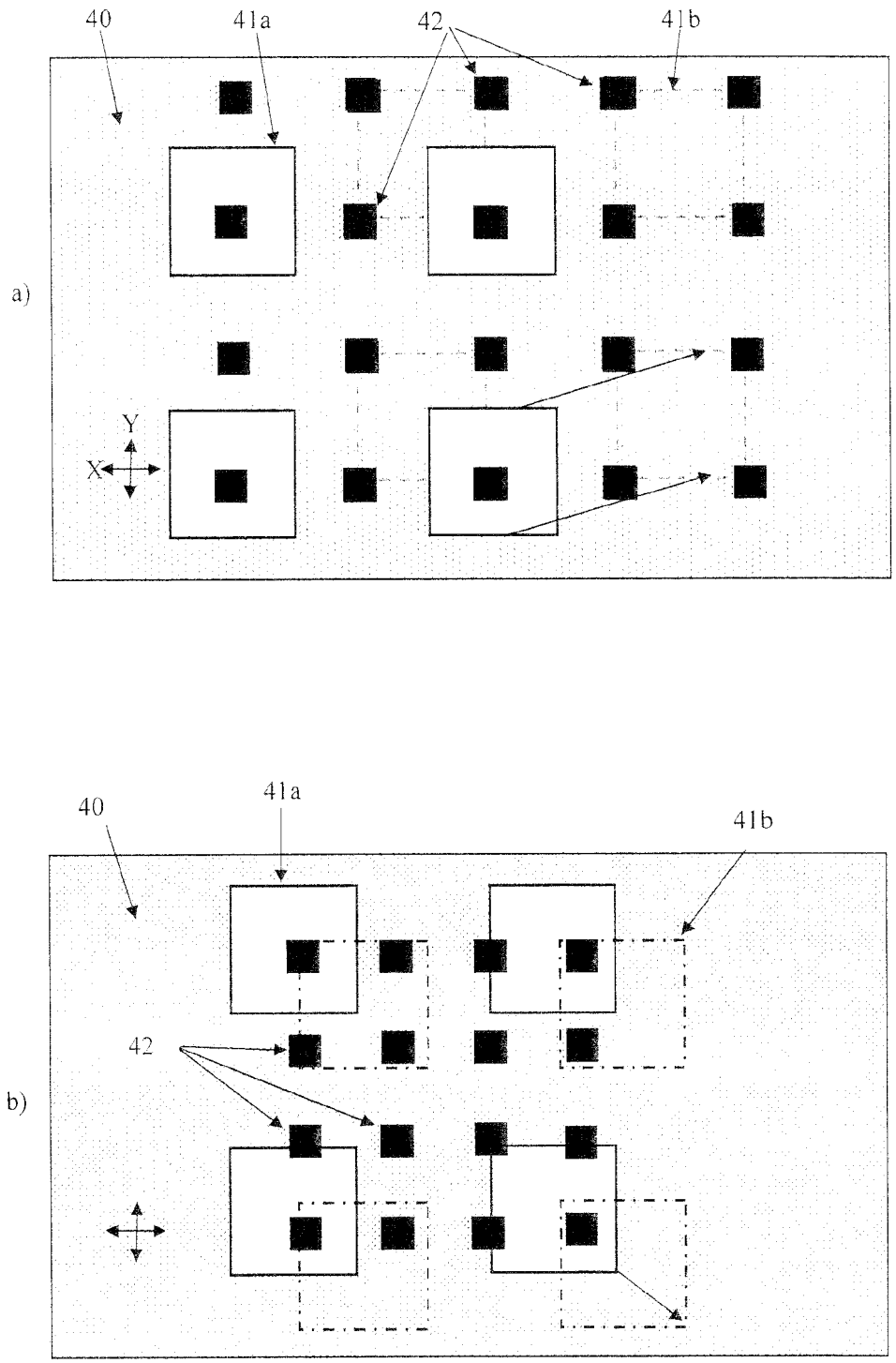
FIG. 6 illustrates a two-dimensional array of fluid chambers overlaying a two-dimensional array of ISFETs.
Figure 7:
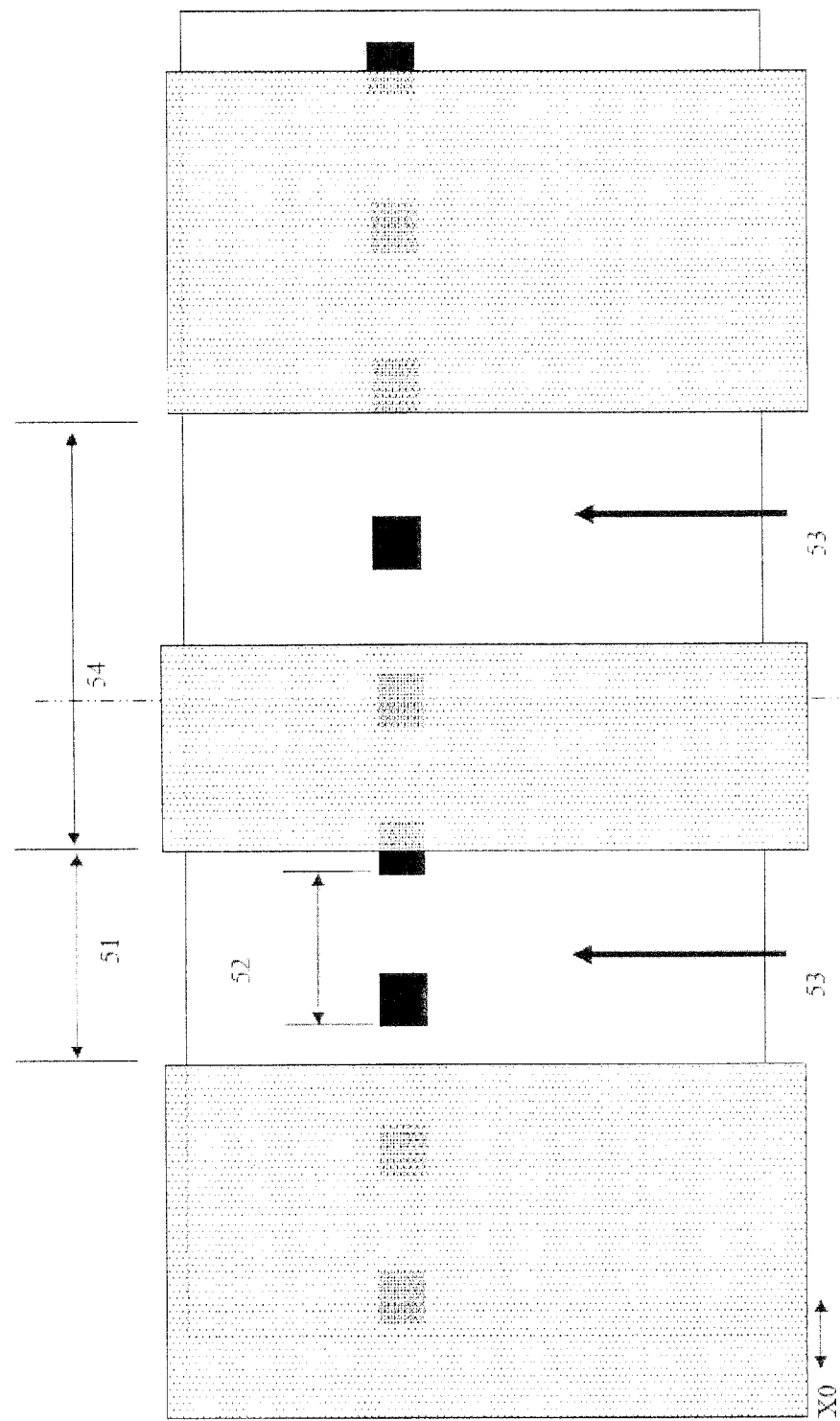
FIG. 7 illustrates a one-dimensional array of fluid chambers overlaying a one-dimensional array of ISFETs.

The array may be one dimensional (see FIG. 7) or two dimensional (see FIG. 6). In FIG. 7, the chambers are part of channels in which a fluid flows (as indicated by the vertical arrows 53). The fluid flow is perpendicular to the sensor array. Movement in the Y-direction has no affect on the sensor-chamber relationship and movement in the X-direction results in a change in the sensor-chamber relationship accounted for by the excess of sensors.

In the embodiment illustrated in FIG. 7, two chambers having a width (51) of 200 um and a pitch (54) of 400 um, intersect a linear array of 50 um-wide ISFETs having a pitch (52) of 150 um. There are 9 sensors, providing an excess of 7 sensors. The channels need not be aligned better than ±475 um from the centre line (allowing a total lateral movement of 950 um) to ensure a whole sensor is exposed to each chamber. Such a tolerance is much improved over the typical device having a single, cantered sensor per chamber where the tolerance would be ±75 nm. However, by adjusting the parameters, even finer channels could be aligned with even less precision. The general expression for the tolerances given by:

$$\text{Total\_Tol} = (Ns-1)*Ps - Ws - (Nc-1)*Pc + Wc \quad (2)$$

$$\pm\text{Tot} = \pm\text{Total\_Tol}/2 \quad (3)$$

where:
- Wc, Ws Width of one chamber, Width of one sensor
- Pc, Ps Pitch of chambers, Pitch of sensors
- Ns, Nc Number of sensors, Number of chambers
- Total_Tol, ±Tol Total allowable lateral movement, alignment tolerance in each direction from centre line An advantage is that this technique decouples the competing priorities of high sensor density and simplicity of assembly, so that fine-pitch sensors and chambers can be employed to minimise chip cost without requiring expensive, fine-scale assembly and alignment.

Certain embodiments may include one or more of the following properties:
- the transverse separation distance between adjacent sensors surfaces is less than the width of chamber in that direction;
- there is a greater number of sensors than number of chambers, preferably 10% more or 2 more;
- there is a greater number of sensors than number of chambers, preferably 50% more or 5 more;
- there is a greater number of sensors than number of chambers, preferably 100% more or 10 more;
- there is at least one sensor at least partly exposed to each chamber and at least one sensor is not wholly exposed to any chamber;
- the width of a chamber is greater than or equal to the pitch of the sensors;
- the pitch of the sensors is less than the pitch of the chambers;
- the pitch of the chambers is twice the pitch of the sensors;
- the pitch of the sensors is less than width of the chambers plus the width of the sensors;
- the total width of the sensor layout is wider than the width of the chamber layout;
- one substrate is aligned to the other substrate within a predetermined tolerance depending on the number of sensors in excess of the number of chambers.

After assembly, it may be initially unknown as to which sensors are covered by the second substrate and which sensors are exposed and to which chamber. Similarly it may be initially unknown which wireless sensors are paired with which receiver on the substrate and located within which chamber The arrangement can become known during an calibration step with controlled conditions to see which sensors measurements are different from the rest. For example, exposed temperature sensors will detect the temperature of the fluid in the chambers whilst blocked sensors will detect the temperature of the substrate. A controlled temperature may be introduced into the substrate or one or more chambers to highlight the difference in sensor measurements. To select an active ISFET, one could change the potential or composition of the fluid electrolyte and observe which ISFETs react. Those that do not react beyond a predetermined threshold are considered to be unexposed to the fluid.

In one embodiment, several wireless sensors communicate with a far field transceiver in the substrate and the identity of each sensor in each chamber is unknown. A property of the fluid in each chamber is altered such that the fluids do not all have the same property in each chamber. For example, a heater in each chamber may be turned on one at a time, or a temperature gradient across the chambers may be established. Alternatively an electrode exposed to the fluid may provide a reference voltage to be detected. The substrate transceiver requests a signal from a particular sensor. This can be repeated for each sensor. The signals of the sensors are compared to each other or to the properties of each chamber fluid to determine which sensors are aligned with which chambers.

Some sensor arrangements will not require controlled conditions. For example, some sensors will output different signals depending on whether they are exposed to a chamber or to the second substrate.

In another embodiment, the relationship between sensors and chamber is determined from the known geometries of the sensor pattern (or substrate receiver pattern) and chamber pattern. Preferably, the signal of the sensor outermost in the array is observed first, moving progressively inwards to detect which is the first signal exposed to a chamber. For example, in FIG. 6a, the bottom-leftmost sensor which appears to be active is determined to be aligned with the bottom-leftmost chamber, the remaining relationships becoming apparent after that. A sensor that is one chamber pitch separated from a known active sensor is likely to be active as well.

In the case where more than one sensor is aligned with a chamber, several active signals from neighbouring sensors will confirm the location of the chamber. The sensor measurements may be used to calculate an average, detect a faulty sensor, or provide measurement redundancy. The plurality of sensors exposed to a chamber may also provide spatio-temporal imagery.

The above calibration steps may be performed using software or hardware. The results of the calibration may be stored in a look up table to identify active sensors and their location for future signal processing. The steps may be performed as an assembly step or during the initial operation of the lab-on-chip.

In the above discussions a fluid is exposed to the sensors by providing a chamber for containing the fluid. The skilled person will appreciate that other microfluidic structures may also provide an appropriate form for exposing the fluid to the sensors such as a channel for directing the fluid across the sensors, a well for holding a fluid, or even a simple substrate for receiving a droplet contained by surface tension. The term "microfluidic" generally refers to the manipulation of fluids that are geometrically constrained to a small, typically submillimeter, scale.

It should be appreciated that features described herein and illustrated in the attached drawings may be incorporated alone or in appropriate combination with other features. For example, different technologies for powering and transmitting signals may be combined to create a wireless sensing system.

The invention claimed is:

1. A device comprising:
   (i) a first substrate defining a plurality of microfluidic structures for receiving a fluid to be sensed and
   (ii) a second substrate comprising or having attached thereto a multiplicity of fluid sensors, the number of sensors being greater than the number of microfluidic structures;
   wherein the second substrate is in contact with the first substrate such that at least one of the sensors is aligned with each microfluidic structure so as to provide an active sensor for each structure, and such that one or more of the sensors is or are not aligned with any microfluidic structure and is or are thereby redundant.

2. The device of claim 1, wherein a distance between adjacent sensors is less than a width of each microfluidic structure.

3. The device of claim 1, wherein the spatial density of sensors is greater than the spatial density of microfluidic structures.

4. The device of claim 1, wherein the sensors are arranged as an array of sensors and the microfluidic structures are arranged as an array of microfluidic structures.

5. The device of claim 4, wherein a width of the sensor array is wider than a width of the microfluidic structure array.

6. The device of claim 4, wherein a pitch of the microfluidic structure array is at least twice a pitch of the sensors array.

7. The device of claim 4, wherein a pitch of the sensor array is less than the width of the microfluidic structure.

8. A configuration apparatus for configuring a device of claim 1, the apparatus comprising:
 (i) the device of claim 1;
 (ii) a receiver for detecting a first signal corresponding to a first sensor; and
 (iii) means for determining which sensors are exposed to which microfluidic structure using knowledge of a property of the fluid in at least one of the microfluidic structures or knowledge of the spatial relationship among the sensors.

9. The configuration apparatus of claim 8, further comprising means for altering the property of the fluid in at least one microfluidic structure.

10. The configuration apparatus of claim 8, further comprising a memory for storing a result of (iii).

11. A method of configuring the device of claim 1, the method comprising:
 (a) detecting a first signal corresponding to a first sensor and
 (b) determining which sensors are exposed to which microfluidic structure using the first signal and knowledge of a property of the fluid of at least one microfluidic structure or knowledge of the spatial relationship among the sensors.

12. The method according to claim 11, further comprising the step of processing the first signal before proceeding to (b) by comparing the first signal to a predetermined value or to a second signal corresponding to a second sensor.

13. The method according to claim 11, further comprising altering the property of the fluid in one or more microfluidic structure.

14. The method according to claim 13, wherein the property of the fluid in each microfluidic structure is altered one microfluidic structure at a time.

15. The method according to claim 11, further comprising performing (a) and (b) for a plurality of the sensors.

16. The method according to claim 15, wherein (a) and (b) are first performed with a sensor located at an extreme of a sensor array, then repeated with sensors that are located progressively inwards.

17. The method according to claim 11, further comprising the step of determining which sensors are not exposed to a microfluidic structure.

18. The method according to claim 11, further comprising creating a look up table identifying which sensors correspond to which microfluidic structures as a result of (b).

19. A method of fabricating a microfluidic sensor device comprising:
 (a) providing a first substrate defining a plurality of microfluidic structures for receiving a fluid to be sensed;
 (b) providing a second substrate comprising or having attached thereto a multiplicity of fluid sensors, the number of sensors being greater than the number of microfluidic structures; and
 (c) fixing the first and second substrates together such that at least one of the sensors is aligned with each microfluidic structure so as to provide an active sensor for each structure, and such that one or more of the sensors is or are not aligned with any microfluidic structure and is or are thereby redundant.

20. The method according to claim 19, wherein misalignment of the first substrate to the second substrate by an amount equal to one sensor pitch from a centre alignment position still results in at least one sensor aligned within each microfluidic structure.

21. The method according to claim 19, wherein misalignment of the first substrate to the second substrate by an amount greater or equal to one channel pitch still results in at least one sensor aligned within each microfluidic structure.

22. The method according to claim 19, wherein the fluid is a biological or chemical sample to be monitored or detected.

* * * * *